(12) United States Patent
Fong

(10) Patent No.: US 8,476,259 B2
(45) Date of Patent: *Jul. 2, 2013

(54) FASUDIL IN COMBINATION THERAPIES FOR THE TREATMENT OF PULMONARY ARTERIAL HYPERTENSION

(75) Inventor: Benson Fong, San Francisco, CA (US)

(73) Assignee: Asahi Kasei Pharma Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/611,849

(22) Filed: Sep. 12, 2012

(65) Prior Publication Data

US 2013/0005711 A1    Jan. 3, 2013

Related U.S. Application Data

(60) Division of application No. 13/005,954, filed on Jan. 13, 2011, which is a continuation of application No. 11/588,185, filed on Oct. 25, 2006, now Pat. No. 7,893,050.

(60) Provisional application No. 60/730,273, filed on Oct. 26, 2005.

(51) Int. Cl.

| A01N 43/00 | (2006.01) |
|---|---|
| A01N 43/16 | (2006.01) |
| A01N 37/08 | (2006.01) |
| A01N 43/36 | (2006.01) |
| A01N 33/02 | (2006.01) |
| A61K 31/551 | (2006.01) |
| A61P 11/00 | (2006.01) |

(52) U.S. Cl.
USPC ...... 514/218; 514/211.07; 514/355; 514/423; 514/460; 514/548

(58) Field of Classification Search
USPC .................... 514/218, 211.07, 355, 423, 460, 514/528
See application file for complete search history.

(56) References Cited

U.S. PATENT DOCUMENTS

| 2,882,271 | A | 4/1959 | Janssen |
|---|---|---|---|
| 3,152,173 | A | 10/1964 | Ehrhart et al. |
| 3,261,859 | A | 7/1966 | Dengel et al. |
| 3,262,977 | A | 7/1966 | Harsányi et al. |
| 3,267,104 | A | 8/1966 | Hermans et al. |
| 3,371,014 | A | 2/1968 | Carlsson et al. |
| 3,485,847 | A | 12/1969 | Bossert et al. |
| 3,562,257 | A | 2/1971 | Kugita et al. |
| 3,773,939 | A | 11/1973 | Janssen |
| 3,799,934 | A | 3/1974 | Meyer et al. |
| 3,962,238 | A | 6/1976 | Mauvernay et al. |
| 3,985,758 | A | 10/1976 | Murakami et al. |
| 4,154,839 | A | 5/1979 | Wehinger et al. |
| 4,220,649 | A | 9/1980 | Kojima et al. |
| 4,264,611 | A | 4/1981 | Berntsson et al. |
| 4,338,322 | A | 7/1982 | Sato |
| 4,446,325 | A | 5/1984 | Ohno et al. |
| 4,466,972 | A | 8/1984 | Neumann |
| 4,567,175 | A | 1/1986 | Takeda et al. |
| 4,572,909 | A | 2/1986 | Campbell et al. |
| 4,663,325 | A | 5/1987 | Ohtaka et al. |
| 4,672,068 | A | 6/1987 | Kutsuma et al. |
| 4,692,464 | A | 9/1987 | Skuballa et al. |
| 4,705,797 | A | 11/1987 | Nardi et al. |
| 4,786,635 | A | 11/1988 | Iwao et al. |
| 4,801,599 | A | 1/1989 | Semeraro et al. |
| 4,808,605 | A | 2/1989 | Branca et al. |
| 4,885,284 | A | 12/1989 | Seto et al. |
| 4,892,875 | A | 1/1990 | Meguro et al. |
| 4,952,592 | A | 8/1990 | Torija et al. |
| 5,292,740 | A | 3/1994 | Burri et al. |
| 6,228,843 | B1 | 5/2001 | Dempsey |
| 7,893,050 | B2 | 2/2011 | Fong |
| 2003/0125321 | A1 | 7/2003 | Bueno |
| 2004/0102361 | A1* | 5/2004 | Bodin ............................... 514/2 |
| 2005/0019314 | A1 | 1/2005 | Bueno |

FOREIGN PATENT DOCUMENTS

| DE | 1 265 758 | 4/1968 |
|---|---|---|
| EP | 0 106 275 | 4/1984 |
| EP | 0 110 553 | 6/1984 |
| EP | 0 870 767 | 10/1998 |
| EP | 0 956 865 | 11/1999 |
| EP | 1 097 711 | 5/2001 |
| EP | 1 541 151 | 6/2005 |
| FR | 1 406 805 | 6/1965 |
| GB | 1 025 578 | 4/1966 |
| JP | 6-141894 | 5/1994 |
| JP | 2001-172182 | 6/2001 |
| WO | 99/18952 | 4/1999 |
| WO | 99/47153 | 9/1999 |
| WO | 00/03746 | 1/2000 |
| WO | 00/56403 | 9/2000 |
| WO | 03/047591 | 6/2003 |
| WO | 2005/030187 | 4/2005 |

OTHER PUBLICATIONS

Fukumoto et al. (Heart, 2005, 91, 391-392).
Harasym (Drug Radio-Dependent Antagonism: A New Category of Multidrug resistance and Strategies for its circumvention, Chapter 13, 2010).

(Continued)

*Primary Examiner* — Sreeni Padmanabhan
*Assistant Examiner* — Uma Ramachandran
(74) *Attorney, Agent, or Firm* — Greenblum & Bernstein, P.L.C.

(57) ABSTRACT

Preferred embodiments of the present invention are related to novel therapeutic drug combinations and methods for treating and/or preventing pulmonary arterial hypertension and/or stable angina. More particularly, aspects of the present invention are related to therapeutic combinations comprising a Rho-kinase inhibitor, such as fasudil, and one or more additional compounds selected from the group consisting of prostacyclins, such as iloprost, endothelin receptor antagonists, PDE inhibitors, calcium channel blockers, 5-$HT_{2A}$ antagonists, such as sarpogrelate, selective serotonin reuptake inhibitors, such as fluoxetine, statins, and vascular remodeling modulators, such as Gleevec.

8 Claims, 3 Drawing Sheets

OTHER PUBLICATIONS

Wilmes (Cancer Chemother Pharmacol 2011, 68, 117-126).
Gitler (Molecular Cancer Therapeutics, 2003, 2, 929-32).
Topics: Primary Pulmonary Hypertension (PPH), Novel Pharmacotherapy; Thrombosis and Circulation vol. 11; No. 4, (2003) with partial translation thereof.
Guilluy Christophe et al., "Inhibition of RhoA/Rho kinase pathway is involved in the beneficial effect of sildenafil on pulmonary hypertension", British Journal of Pharmacology Dec. 2005 LNKD-PUBMED;16205723, vol. 146, No. 7, XP002640064, Oct. 3, 2005, pp. 1010-1018.
"Advancing Therapy for Pulmonary Arterial Hypertension Can Animal Models Help?", American Review of Respiratory Disease, New York, NY, US, vol. 169, No. 1, XP008041696, Jan. 1, 2004, pp. 5-6.
Rajasekaran Mahadevan et al., "Rho-Kinase inhibition improves erectile function in aging male Brown-Norway rats.", Journal of Andrology Mar.-Apr. 2005 LNKD-PUBMED: 15713824, vol. 26, No. 2, XP002640066, Mar. 2005, pp. 182-188.
Search report from E.P.O. that issued with respect to European Patent Application No. 11000632.7, mail date is Jun. 27, 2011.
D'Alonzo, G. E. et al. "Survival in Patients with Primary Pulmonary Hypertension"; 1991 Ann Intern Med 115:343-349.
Palevsky, H. I. et al."Primary Pulmonary Hypertension. Vascular Structure, morphometry, and Responsiveness to vasodilator Agents"; 1989 Circulation 80:1207-1221.
Rubin, L. J. "Primary Pulmonary Hypertension"; 1997 N Engl J Med 336:111-117.
Wagenvoort, C. A. & Wagenvoort, N. "Primary Pulmonary Hypertension A Pathologic Study of the Lung Vessels in 156 Clinically Diagnosed Case"; 1970 Circulation 42:1163-1184.
Wood, P. "Pulmonary Hypertension with Special Reference to the vasoconstrictive Factor"; 1958 Br Heart J 20:557-570.
Giaid, A. & Saleh, D. "Reduced Expression of Endothelial Nitric Oxide Synthase in the Lungs of Patients with Pulmonary Hypertension"; 1995 N Engl J Med 333:214-221.
Xue, C & Johns, R. A. "Endothelial Nitric oxide Synthase in the Lungs of Patients with Pulmonary Hypertension;" 1995 N Engl J Med 333:1642-1644.
Abe, K. et al., "Long Term Treatment with a Rho-Kinase Inhibitor Improves Monocrotaline-Induced Fatal Pulmonary Hypertension in Rats"; 2004 Circ. Res. 94:385-393.
Fagan, K. A. et al. "Attenuation of acute hypoxic pulmonary vasoconstriction and hypoxic pulmonary hypertension in mice by inhibition of Rho-kinase"; 2004 Am. J. Physiol. Lung Cell. Mol. Physiol. 287:L656-L664.
Nagaoka et al. "Rho/Rho kinase signaling mediates increased basal pulmonary vascular tone in chronically hypoxic rats"; 2004 Am. J. Physiol. Lung Cell Mol. Physiol. 287:L665-L672.
Nagaoka et al. "Inhaled Rho Kinase Inhibitors Are Potent and Selective Vasodilators in Rat Pulmonary Hypertension"; 2005 Am. J. Respir. Crit. Care Med. 171:494-499.
Van Aelst & D'Souza-Schorey. "Rho GTPases and signaling networks";1997 Genes Dev. 11:2295-2322.
Sauzeau et al. "Cyclic GMP-dependent Protein Kinase Signaling Pathway Inhibits RhoA-induced $Ca^{2+}$ Sensitization of Contraction in Vascular Smooth Muscle"; 2000 J. Biol. Chem. 275:21722-21729.
Gudi et al. "cGMP-dependent Protein Kinase Inhibits Serum-response Element-dependent Transcription by Inhibiting Rho Activation and Functions"; 2002 J. Biol. Chem. 277:37382-37393.
Robertson et al. "Inhibition of sustained hypoxic vasoconstriction by Y-27632 in isolated intrapulmonary arteries and perfused lung of the rat"; 2000 Br. J. Pharmacol. 131:5-9.
Wang et al. "Rho-Kinase Activation Is Involved in Hypoxia-Induced Pulmonary Vasoconstriction"; 2001 Am. J. Respir. Cell Mol. Biol. 25:628-635.
Wilson et al. "Mechanical Strain Induces Growth of Vascular Smooth Muscle Cells via Autocrine Action of PDGF"; 1993 J. Cell Biol. 123:741-747.
Liu et al. "Rho Kinase—Induced Nuclear Translocation of ERK1/ERK2 in Smooth Muscle Cell Mitogenesis Caused by Serotonin"; 2004 Circ. Res. 95: 579-586; including online supplement pp. 1-15.

Takemoto et al. "Rho-Kinase Mediates Hypoxia-Induced Downregulation of Endothelial Nitric Oxide Synthase"; 2002 Circulation 106; 57-62.
Uehata et al. "Calcium sensitization of smooth muscle mediated by a Rho-associated protein kinase in hypertension"; 1997, Nature 389:990-994.
Shimokawa, H. et al. "Rho-kinase-mediated pathway induces enhanced myosin light chain phosphorylations in a swine model of coronary artery spasm"; 1999 Cardiovasc. Res. 43:1029-1039.
Sasaki et al. "The novel and specific Rho-kinase inhibitor (S)-(+)-2-methy1-1-[(4-methyl-5-isoquinoline) sulfony1]-homopiperazine as a probing molecule for Rho-kinase-involved pathway"; 2002 Pharmacol Ther. 93:225-32.
Tamura et al. "Development of specific Rho-kinase inhibitors and their clinical application"; 2005 Biochim. Biophys. Acta; 1754 (1-2), 245-252.
Shimokawa and Takeshita. "Rho-Kinase Is an Important Therapeutic Target in Cardiovascular Medicine"; 2005 Arterioscler Thromb Vasc Biol 25:1767-1775.
Hirooka and Shimokawa. "Therapeutic Potential of Rho-Kinase Inhibitors in Cardiovascular Diseases"; 2005 Am J Cardiovasc Drugs 5(1): 31-39.
Tramontano et al. "Statin decreases endothelial microparticle release from human coronary artery endothelial cells: implication for the Rho-kinase pathway"; 2004 Biochem Biophys Res Comm 320:34-38.
Ohnaka et al. "Pitavastatin Enhanced BMP-2 and Osteocalcin Expression by Inhibition of Rho-Associated Kinase in Human Osteoblasts"; 2001 Biochem Biophys Res Comm 287: 337-342.
Barst, R. J. et al. "A Comparison of Continuous Intravenous Epoprostenol (Prostacyclin) with Conventional Therapy for Primary Pulmonary Hypertension"; 1996 N Engl J Med 334:296-301.
Badesch, D. B. et al. "Continuous Intravenous Epoprostenol for Pulmonary Hypertension Due to the Scleroderma Spectrum of Disease"; 2000 Ann Intern Med 132:425-434.
Walmrath, D. et al. "Aerosolised prostacyclin in adult respiratory distress syndrome"; 1993 Lancet 342:961-962.
Walmrath, D. et al. "Effects of Aerosolized Prostacyclin in Severe Pneumonia: Impact of Fibrosis"; 1995 Am J Respir Crit Care Med 151:724-730.
Walmrath, D. et al. "Direct Comparison of Inhaled Nitric Oxide and Aerosolized Prostacyclin in Acute Respiratory Distress Syndrome"; 1996 Am J Respir Crit Care Med 153:991-996.
Zwissler, B. et al. "Inhaled Prostacyclin (PGI2) versus Inhaled Nitric Oxide in Adult Respiratory Distress Syndrome"; 1996 Am J Respir Crit Care Med 154:1671-1677.
Olschewski, H. et al. "Inhaled Prostacyclin and Iloprost in Severe Pulmonary Hypertension Secondary to Lung Fibrosis";1999 Am J Respir Crit Care Med 160:600-607.
Barst, R. J. et al. "Beraprost Therapy for Pulmonary Arterial Hypertension"; 2003 J. Am. Coll. Cardiol. 41:2119-25.
Fitscha, P. et al. "Effect of Iloprost on In Vivo and In Vitro Platelet Function in Patients with Peripheral Vascular Disease (PVD)"; 1987 Adv Prostaglandin Thromboxane Leukot Res 17:450-454.
Hoeper, M. M. et al. "A Comparison of the Acute Hemodynamic Effects of Inhaled Nitric Oxide and Aerosolized Iloprost in Primary Pulmonary Hypertension"; 2000 J Am Coll Cardiol 35:176-182.
Olschewski, H. et al. "Aerosolized Prostacyclin and Iloprost in Severe Pulmonary Hypertension"; 1996 Ann Intern Med 124:820-824.
Gessler, T. et al. "Ultrasonic versus jet nebulization of iloprost in severe pulmonary hypertension"; 2001 Eur Respir J 17:14-19.
Wensel, R. et al. "Effects of Iloprost Inhalation on Exercise Capacity and Ventilatory Efficiency in Patients With Primary Pulmonary Hypertension;" 2000 Circulation 101:2388-2392.
Hoeper, M. M. et al. "Long-term Treatment of Primary Pulmonary Hypertension with Aerosolized Iloprost, a Prostacyclin Analogue"; 2000 N Engl J Med 342:1866-1870.
Olschewski, H. et al. "Recovery from circulatory shock in severe primary pulmonary hypertension (PPH) with aerosolization of iloprost";1998 Intensive Care Med 24:631-634.

Stricker, H. et al. "Sustained improvement of performance haemodynamics with long-term aerosolised prostacyclin therapy in severe pulmonary hypertension;" 1999 Schweiz Med Wochenschr 129:923-927.

Olschewski, H. et al. "Inhaled Iloprost to Treat Severe Pulmonary Hypertension: An Uncontrolled Trial;" 2000 Ann Intern Med 132:435-443.

Beghetti, M. et al. Long term inhalation of iloprost in a child with primary pulmonary hypertension: an alternative to continuous infusion'; 2001 Heart 86:e10, 1-2.

Olschewski, H et al. "Inhaled Iloprost for Severe Pulmonary Hypertension;" 2002 N Engl J Med 347:322-329.

Doggrell, S. A. "Sarpogrelate: cardiovascular and renal clinical potential"; 2004 Expert Opin. Investig. Drugs 13(7), 865-874.

Miyata, M. et al. "Development of Monocrotaline-Induced Pulmonary Hypertension Is Attenuated by a Serotonin Receptor Antagonist"; 2000 Lung 178:63-73.

Hironaka, E. et al. "Serotonin receptor antagonist inhibits monocrotaline-induced pulmonary hypertension and prolongs survival in rats"; 2003 Cardiovasc. Res. 60:692-699.

Miyata, M. et al. "Effect of a Serotonin Receptor Antagonist on Interleukin-6-Induced Pulmonary Hypertension in Rats"; 2001 Chest 119:554-561.

Saini, H. K. et al. "Therapeutic Potentials Sarpogrelate in Cardiovascular Disease"; 2004 Cardiovascular Drug Rev. 22:27-54.

Setoguchi, Y. et al. Effects of Chronic Administration of Sarpogrelate on Systolic Blood Pressure of Spontaneously Hypertensive Rats: Comparison with Quinapril'; 2002 Pharmacol. 64:71-75.

Kato, S. et al. "Suppressive effect of saprogrelate hydrochloride on Raynaud's phenomenon and respiratory failure in patients with systemic sclerosis"; 2000 Respirology 5:27-32.

Kato, S. et al. "Suppressive Effect of Saprogrelate Hydrochloride on Respiratory Failure and Right Ventricular Failure with Pulmonary Hypertension in Patients with Systemic Sclerosis"; 2000 J. Int. Med. Res. 28:258-268.

Kinugawa et al. "Effectiveness of a novel serotonin blocker, Sarpogrelate, for patients with angina pectoris"; 2002 Am Heart J; 144:e1.

Channick, R. N. et al. "Effects of the dual endothelin-receptor antagonist bosentan in patients with pulmonary hypertension: a randomised placebo-controlled study"; 2001 Lancet 358:1119-1123.

Rubin, L. J. et al. "Bosentan Therapy for Pulmonary Arterial Hypertension"; 2002 N Engl J Med 346:896-903.

Barst, R. J. et al. Efficacy and Safety of Chronic Treatment with the Oral Selective Endothelin-A Receptor Blocker Sitaxsentan in Pulmonary Arterial Hypertension (PAH); Abstract 2076; Abstracts from Scientific Sessions 2000, II-427.

Nagaya, N. et al. "Short-term Oral Administration of L-Arginine Improves Hemodynamics and Exercise Capacity in Patients with Precapillary Pulmonary Hypertension"; 2001 Am J Respir Crit Care Med 163:887-891.

Michelakis, E. et al. "Oral Sildenafil Is an Effective and Specific Pulmonary Vasodilator in Patients With Pulmonary Arterial Hypertension: Comparison With Inhaled Nitric Oxide;" 2002 Circulation 105:2398-2403.

Ghofrani, H. et al. "Sildenafil for treatment of lung fibrosis and pulmonary hypertension: a randomized controlled trial"; 2002 Lancet 360:895-900.

Schermuly, R. T. et al. "Subthreshold Doses of Specific Phosphodiesterase Type 3 and 4 Inhibitors Enhance the Pulmonary Vasodilatory Response to Nebulized Prostacyclin with Improvement in Gas Exchange"; 2000 J Pharmacol Exp Ther 292:512-20.

Ghofrani et al. "Combination Therapy with Oral Sildenafil and Inhaled Iloprost for Severe Pulmonary Hypertension"; 2002 Ann Intern Med 136:515-22.

Ghofrani et al. "Oral Sildenafil as Long-Term Adjunct Therapy to Inhaled Iloprost in Severe Pulmonary Arterial Hypertension"; 2003 J am Coll Cardiol 42: 158-164.

Oka, Masahiko. "Phosphodiesterase 5 inhibition restores impaired ACh relaxation in hypertensive conduit pulmonary arteries"; 2001 Am J Physiol Lung Cell Mol Physiol 280: L432-L435.

Yoshiteru et al. "$Ca^{2+}$ release from ryanodine-sensitive store contributes to mechanism of hypoxic vasoconstriction in rat lungs;" 2002 J Appl Physiol 92: 527-534.

Fukumoto et al; "Acute vasodilator effects of a Rho-kinase inhibitor, fasudil, in patients with severe pulmonary hypertension"; 2005 Heart 91:391-392.

Hoeper, M. M. et al. "Bosentan treatment in patients with primary pulmonary hypertension receiving nonparenteral prostaglandins"; 2003 Am J Respir Crit Care Med 167:A275-EOA.

Extended European Search Report issued in connection with EP 09 00 7232.3, dated Sep. 2, 2009.

Chem. Abs., vol. 131, Abs No. 125180, 1999.

Dashwood et al., "[$^3$H]Bosentan binding to human coronary artery: functional correlates"*Journal of Cardiovascular Pharmacology* vol. 26, Suppl. 3, pp. S376-S379, 1995.

Shimokawa et al. (Circulation Research, 2004, 94, 385-93).

"Advancing therapy for pulmonary arterial hypertension: can animal models help?" American Review of Respiratory Disease, New York, NY 169:506, 2004.

Abe, K. et al. (2005) "Prostacycling does not inhibit rhhibit rho-kinase: an implication for the treatment of pulmonary hypertension"Cardiovasc. Pharmacol. 45:120-124.

Channick R. et al. (2000) "Combination therapy for pulmonary hyptertension: a glimpse into the future?" Crit. Care Med. 28:896-897.

Channick, R. et al. (2001) "New and experimental therapies for pulmonary hypertension" Clinics in Chest Medicine 22:539-545.

Fukumoto, Y. et al. (2007) "Acute vasodilator effects of a rho-kinase inhibitor, fasudil, in patients with severe pulmonary hypertension" Heart 91:391-392.

Hoeper, M. et al. (2002) "New treatments for pulmonary arterial hypertension" American Journal of Respirary and Critical Care Medicine, American Lung Association 165:1209-1216.

Hyvelin, J-M. et al. (2005) "Inhibition of rho-kinase attenuates hypoxia-induced angiogenesis in the pulmonary circulation" Circulation Research 97:185-191.

Molnar, C. et al. (2204) "Successful switch from inhalative iloporost to oral bosentan in portopulmonary hypertension associated with liver cirrhosis" Wien Klin Wochenschr. 116/17-18:627-630.

Olschewski, H. et al. (2002) "Pulmonaler hochdruck pulmonary hypertension" Internist, 43: 1498-1509.

Partial International Search Report from corresponding PCT application No. PCT/US2006/041830.

Riondino, S. et al. (2002) "Convulxin induces platelet shape change through myosin light chain kinase and rho kinase" Eur. J. Biochem. 269:5878-5884.

Weitzenblum, E. et al. (2004) "Actualite sur l'hypertension arterielle pulmonaire (htap) << idiopathique>>update on idiopathic pulmonary arterial hypertension" Revue des maladies respiratoires, Paris, FR 21:7S82-7S83.

* cited by examiner

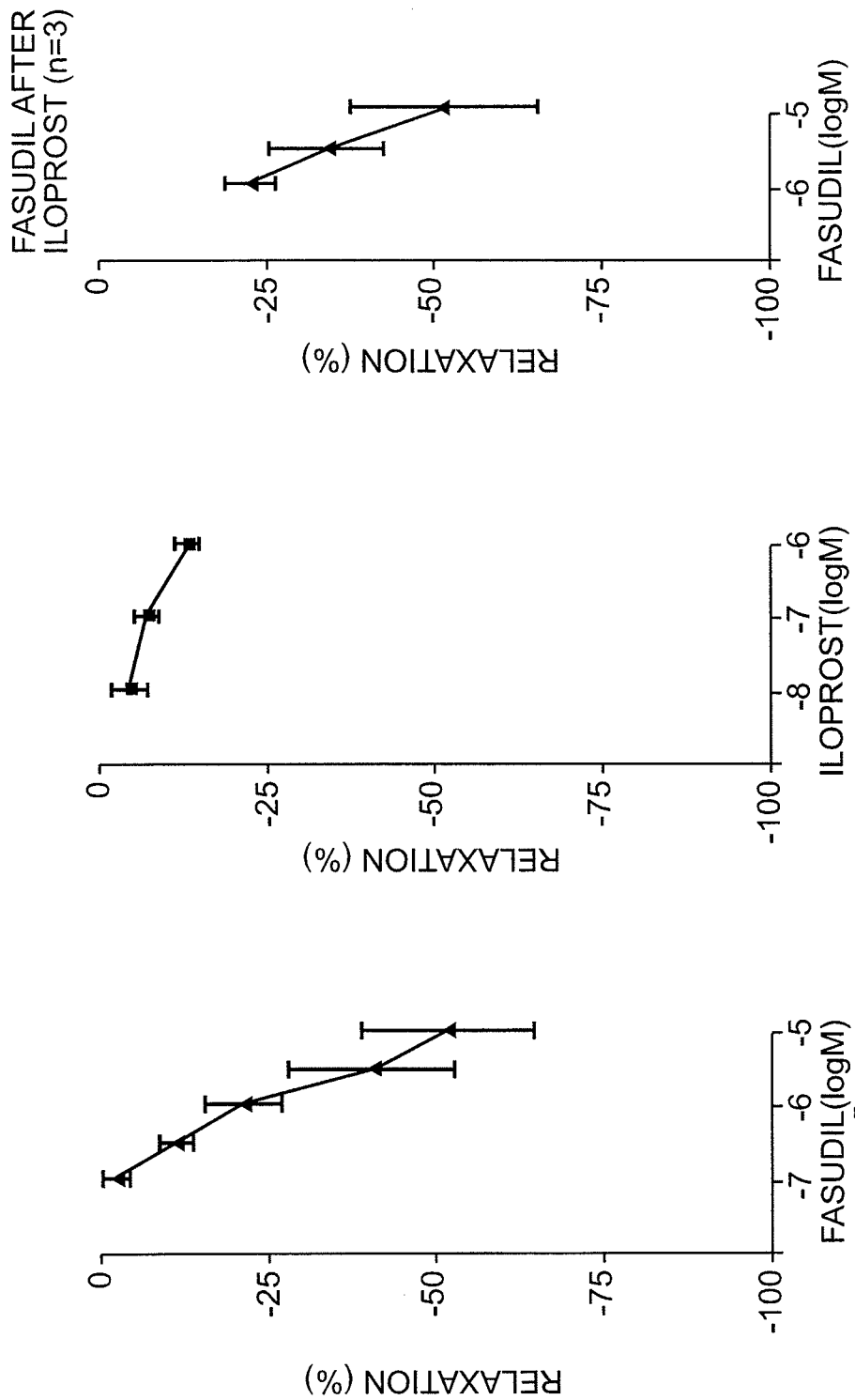

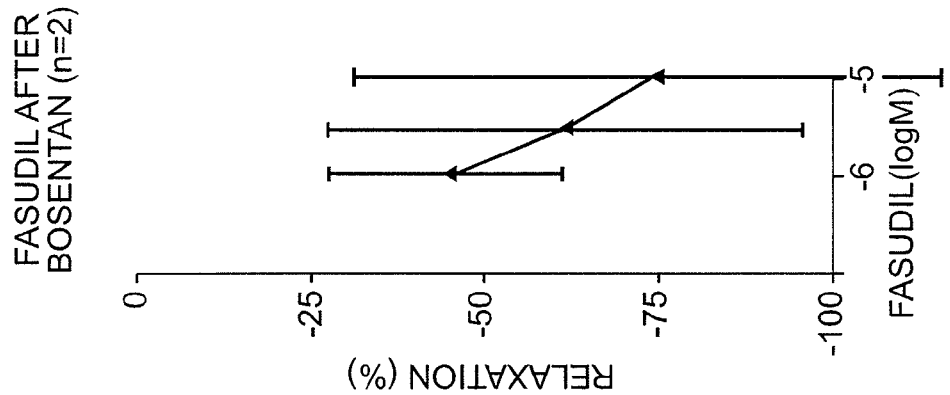
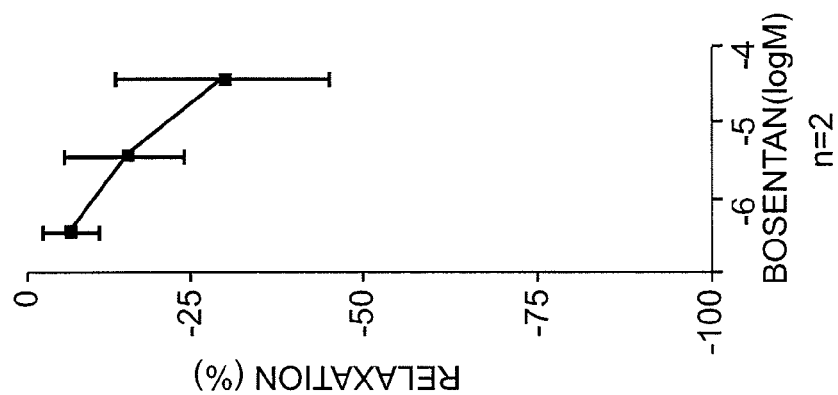
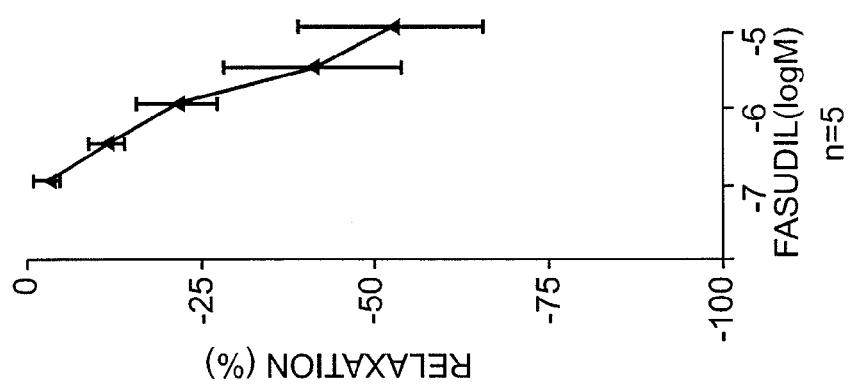

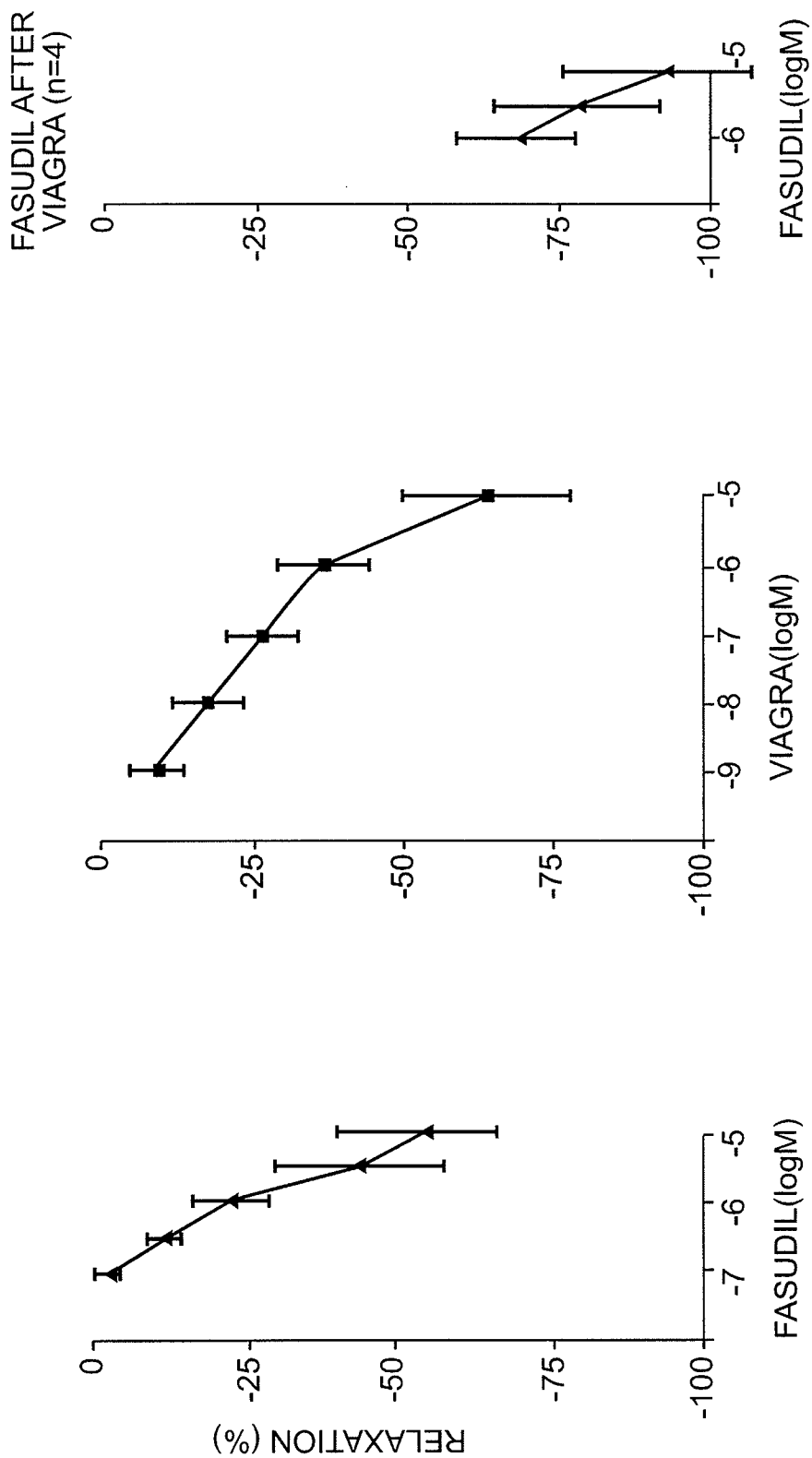

FASUDIL IN COMBINATION THERAPIES FOR THE TREATMENT OF PULMONARY ARTERIAL HYPERTENSION

RELATED APPLICATIONS

The present application is a divisional of pending U.S. patent application Ser. No. 13/005,954, filed on Jan. 13, 2011, which is a continuation of U.S. patent application Ser. No. 11/588,185, filed on Oct. 25, 2006, now U.S. Pat. No. 7,893,050, which claims the benefit of U.S. Provisional Patent Application No. 60/730,273, filed on Oct. 26, 2005. The disclosures of application Ser. Nos. 13/005,954, 11/588,185 and 60/730,273 are incorporated by reference herein in their entireties.

FIELD OF THE INVENTION

Embodiments of this invention are related to therapeutic formulations and methods of using Rho-kinase inhibitors, such as fasudil, in combination with a prostacyclin or prostacyclin agonist, such as iloprost for treating and/or preventing pulmonary arterial hypertension ("PAH"). In other preferred embodiments, the Rho-kinase inhibitor may be used in therapeutic combinations with other agents, such as for example, endothelin receptor antagonists, PDE inhibitors, calcium channel blockers, 5-HT$_{2A}$ antagonists (such as sarpogrelate), selective serotonin reuptake inhibitors (such as fluoxetine), statins, and vascular remodeling modulators (such as Gleevec) for the treatment and/or prevention of PAH and/or stable angina.

BACKGROUND OF THE INVENTION

Pulmonary arterial hypertension is a debilitating disease characterized by an increase in pulmonary vascular resistance leading to right ventricular failure and death. PAH with no apparent cause is termed primary pulmonary hypertension ("PPH"). Recently, various pathophysiological changes associated with this disorder, including vasoconstriction, vascular remodeling (i.e. proliferation of both media and intima of the pulmonary resistance vessels), and in situ thrombosis have been characterized (e.g., D'Alonzo, G. E. et al. 1991 *Ann Intern Med* 115:343-349; Palevsky, H. I. et al. 1989 *Circulation* 80:1207-1221; Rubin, L. J. 1997 *N Engl J Med* 336:111-117; Wagenvoort, C. A. & Wagenvoort, N. 1970 *Circulation* 42:1163-1184; Wood, P. 1958 *Br Heart J* 20:557-570). Impairment of vascular and endothelial homeostasis is evidenced from a reduced synthesis of prostacyclin (PGI$_2$), increased thromboxane production, decreased formation of nitric oxide and increased synthesis of endothelin-1 (Giaid, A. & Saleh, D. 1995 *N Engl J Med* 333:214-221; Xue, C & Johns, R. A. 1995 *N Engl J Med* 333:1642-1644). The intracellular free calcium concentration of vascular smooth muscle cells of pulmonary arteries in PPH has been reported to be elevated.

The pathogenesis of pulmonary hypertension ("PH") is a complex and multifactorial process. Pathologic changes of pulmonary arteries, which involve endothelial dysfunction, endothelial and smooth muscle cell proliferation, and increased vasoconstriction, decrease the lumen area of the pulmonary microvasculature, causing fixed elevation of pulmonary vascular resistance. Although these pathological features are common to all forms of human PH, the mechanisms responsible for this abnormal vascular proliferation are unknown. However, impairment of endothelial functions leading to an imbalance of vasodilator and vasoconstrictor influences is likely to play a central role in the initiation and progression of PH. Drugs that improve the endothelial function or restore the altered balance of endothelium-derived vasoactive mediators such as endothelin-1 receptor antagonists and prostacyclin analogues are used to treat this disease with moderate success. The NO/cGMP axis is also considered as a major target for the treatment of PH. Recently, the type 5 phosphodiesterase inhibitor sildenafil has been identified as a promising therapeutic agent for PH. The type 5 phosphodiesterase is the major cGMP-degrading phosphodiesterase in the pulmonary vasculature and is upregulated in PH. Sildenafil reduces right ventricular hypertrophy in chronic hypoxic mice, pulmonary arterial pressure in chronic hypoxic rats, and improves survival rate in rats with PH induced by monocrotaline injection. Short-term studies in patients with PH suggest that sildenafil is an effective pulmonary vasodilator.

On the other hand, recent pharmacological studies have suggested a role for the serine/threonine kinase Rho kinase in the development of PH. In vivo, intravenous or oral treatment with Rho kinase inhibitor (Y-27632 or fasudil) nearly normalizes the high pulmonary arterial pressure in chronically hypoxic rats, attenuates the development of chronic hypoxia-induced PH in mice, and reduces pulmonary arterial lesions in the model of monocrotaline-induced PH in rats (Abe K. et al. 2004 *Circ. Res.* 94:385-393; Fagan K. A. et al. 2004 *Am. J. Physiol. Lung Cell. Mol. Physiol.* 287:L656-L664; Nagaoka et al., 2004 *Am. J. Physiol. Lung Cell Mol. Physiol.* 287:L665-L672). In addition, inhaled Y-27632 or fasudil causes sustained and selective pulmonary vasodilation in monocrotaline-induced PH and in spontaneous PH in fawn-hooded rats, as well as in chronically hypoxic rats (Nagaoka et al. 2005 *Am. J. Respir. Crit. Care Med.* 171:494-499). Rho kinase is one of the main downstream effectors of the small G protein RhoA, which functions as a tightly regulated molecular switch that governs a wide range of cellular functions (Van Aelst & D'Souza-Schorey, 1997 *Genes Dev.* 11:2295-2322). In particular, Rho kinase phosphorylates the myosin phosphatase target subunit 1 (MYPT1) of smooth muscle myosin phosphatase at Thr-696, leading to the inhibition of its activity. This inhibition of smooth muscle myosin phosphatase activity is a primary mechanism of the Ca$^{2+}$ sensitization of smooth muscle contraction. A large body of evidence has now been obtained regarding the important functions of RhoA in the vasculature, and RhoA has been shown to play a major role in the regulation of vascular cell processes such as actin cytoskeleton organization, contraction, gene expression, and differentiation. In vascular smooth muscle cells, RhoA has been shown to be regulated by the NO/cGMP pathways. RhoA is phosphorylated by cGMP-dependent protein kinase (PKG) (Sauzeau et al., 2000 *J. Biol. Chem.* 275:21722-21729). This phosphorylation prevents the translocation of active GTP-bound RhoA to the membrane, which is an obligatory step for the activation of its downstream effectors. Activation of the NO/cGMP pathway thus leads to the inhibition of RhoA-dependent functions, including actin cytoskeleton organization, Ca$^{2+}$ sensitization of the contraction, and gene transcription (Sauzeau et al., 2000 *J. Biol. Chem.* 275: 21722-21729; Gudi et al., 2002 *J. Biol. Chem.* 277:37382-37393). The beneficial effect of Rho kinase inhibitor on PH could be ascribed to multiple mechanisms, including its inhibitory effect on pulmonary vasoconstriction (Robertson et al., 2000 *Br. J. Pharmacol.* 131:5-9; Wang et al., 2001 *Am. J. Respir. Cell Mol. Biol.* 25:628-635; Nagaoka et al., 2004 *Am. J. Physiol. Lung Cell Mol. Physiol.* 287:L665-L672), the prevention of mechanical stress-induced expression of growth factors (Wilson et al., 1993 *J. Cell Biol.* 123:741-747), or the inhibition of Rho kinase-mediated mitogenic effects of serotonin (Liu et al., 2004 *Circ. Res.* 95: 579-586) and Rho kinase-mediated inhibition of nitric oxide synthase (Takemoto et al., 2002 *Circulation* 106: 57-62).

Current therapies for pulmonary hypertension are unsatisfactory. These typically involve calcium channel antagonists, prostacyclins, endothelin receptor antagonists and long-term anticoagulant therapy. However, each treatment has limitations and side effects.

Consequently there is a long felt need for a new and combined medicament for the treatment of PAH, preferably employing lower doses of the active agents, which exhibits fewer or no adverse effects (i.e., less toxicity) and a favorable profile in terms of effectiveness in patients in different stages of PAH.

SUMMARY OF THE INVENTION

A therapeutic combination is disclosed herein for the treatment and/or prevention of PAH and/or angina. The disclosed combinations comprise an effective amount of a Rho-kinase inhibitor and at least one additional compound selected from the group consisting of prostacyclins, endothelin receptor antagonists, PDE inhibitors, calcium channel blockers, $5\text{-}HT_{2A}$ antagonists, selective serotonin reuptake inhibitors, statins, and vascular remodeling modulators.

In preferred embodiments, the Rho-kinase inhibitor is selected from the group consisting of fasudil, H-1152P, and Y-27632.

In preferred embodiments, the prostacyclin is selected from the group consisting of iloprost, treprostinol, and beraprost.

In preferred embodiments, the endothelin receptor antagonist is selected from the group consisting of bosentan, sitaxentan, and ambrisentan.

In preferred embodiments, the PDE inhibitor is selected from the group consisting of enoximone, milrinone, amrinone, sildenafil, tadalafil and vardenafil.

In preferred embodiments, the calcium channel blocker is selected from the group consisting of amlodipine, diltiazem, isradipine, nicardipine, nifedipine, nimodipine, nisoldipine, nitrendipine, and verapamil.

In preferred embodiments, the $5\text{-}HT_{2A}$ antagonist is sarpogrelate.

In preferred embodiments, the selective serotonin reuptake inhibitor is selected from the group consisting of fluoxetine, sertrlaine, paroxetine and venlafaxine.

In preferred embodiments, the statin is selected from the group consisting of fluvastatin, pitavastatin, pravastatin and atorvastatin.

In preferred embodiments, the vascular remodeling modulator is Gleevec.

In preferred embodiments, the Rho-kinase inhibitor and at least one additional compound may be formulated together or independently.

Most preferably, the Rho-kinase inhibitor is fasudil.

The fasudil may be formulated for administration via inhalation. For example, the fasudil may be formulated in a dry powder or an aerosolizable solution.

A therapeutic combination is disclosed in accordance with one preferred embodiment. The combination comprises fasudil and iloprost or salts thereof, wherein the fasudil and iloprost or salts thereof are provided in amounts which together are sufficient to treat and/or prevent at least one symptom associated with PAH. At least one of fasudil and iloprost are preferably formulated for administration by inhalation. Alternatively, both fasudil and iloprost may be formulated for administration by inhalation. In preferred combinations, at least one additional compound is included, selected from the group consisting of endothelin receptor antagonists, PDE inhibitors, calcium channel blockers, selective serotonin reuptake inhibitors, statins, and vascular remodeling modulators.

Another therapeutic combination is disclosed, comprising fasudil and sarpogrelate or salts thereof, wherein the fasudil and sarpogrelate or salts thereof are provided in amounts which together are sufficient to treat and/or prevent at least one symptom associated with PAH and/or stable angina. Preferably, at least one of fasudil and sarpogrelate are formulated for administration by inhalation. Alternatively, both fasudil and sarpogrelate are formulated for administration by inhalation. In preferred combinations, at least one additional compound is included, selected from the group consisting of endothelin receptor antagonists, PDE inhibitors, calcium channel blockers, selective serotonin reuptake inhibitors, statins, and vascular remodeling modulators.

A method of treating and/or preventing PAH and/or stable angina is also disclosed. The method comprises administering effective amounts of the therapeutic combination of Claim 1.

BRIEF DESCRIPTION OF THE DRAWINGS

FIG. 1 (A, B and C) shows dose response curves of effects of fasudil (A), iloprost (B) and fasudil after iloprost, $10^{-6}$ M (C) on relaxation of vasoconstricted small pulmonary arteries rings.

FIG. 2 (A, B and C) shows dose response curves of effects of fasudil (A), bosentan (B) and fasudil after bosentan, $5\times10^{-5}$ M (C) on relaxation of vasoconstricted small pulmonary arteries rings.

FIG. 3 (A, B and C) shows dose response curves of effects of fasudil (A), Viagra™ (B) and fasudil after Viagra™, $10^{-5}$ M (C) on relaxation of vasoconstricted small pulmonary arteries rings.

DETAILED DESCRIPTION OF THE PREFERRED EMBODIMENTS

In an embodiment of the present invention, a combination therapy is disclosed for treating and/or preventing PAH. In one preferred embodiment, the combination therapy comprises a therapeutically effective amount of a Rho-kinase inhibitor, and most preferably fasudil, in combination with a therapeutically effective amount of at least one additional active agent. In one embodiment, the Rho-kinase inhibitor is combined with a prostacyclin, most preferably, iloprost. In another embodiment, the Rho-kinase inhibitor and prostacyclin are further combined with one or more additional active agents. The active agents may be formulated and administered together or may be formulated and administered independently. For example, the at least one additional active agent may be formulated together with the Rho-kinase inhibitor in a single tablet or capsule, a single dry powder formulated for inhalation, or a solution formulated for aerosolization and inhalation. Any of the additional agents may be formulated and administered separately from the Rho-kinase inhibitor. In one preferred embodiment, the Rho-kinase inhibitor is aerosolized. In one preferred embodiment, the Rho-kinase inhibitor is administered by any route, and a prostacyclin is administered by inhalation, e.g., dry powder or aerosolized formulation. In one preferred embodiment, therapeutically effective amounts of both fasudil and iloprost are combined and administered together via inhalation in dry powder or aerosol form.

In one embodiment, the Rho-kinase inhibitor may be combined with one or more additional active agents selected from the group consisting of prostacyclins, endothelin receptor antagonists, PDE inhibitors, calcium channel blockers, 5-HT$_{2A}$ antagonists, selective serotonin reuptake inhibitors, statins, and vascular remodeling modulators. Preferably, the one or more additional active agents used in the therapeutic combination modulates pulmonary arterial pressure through a mechanism which is distinct from that of fasudil. Preferably, the prostacyclin is selected from the group consisting of treprostinol (Remodulin®, United Therapeutics), beraprost, and iloprost (Ventavis®). Preferably, the endothelin receptor antagonist is selected from the group consisting of bosentan (Tracleer™, Actelion), ambrisentan (Myogen) and sitaxentan (Encysive Pharmaceuticals). Preferably, the PDE inhibitor is selected from the group consisting of enoximone, milrinone (Primacor®), amrinone (Inocor®), sildenafil (Viagra®), tadalafil (Cialis®) and vardenafil (LEVITRA®). Preferably, the calcium channel blocker is selected from the group consisting of amlodipine, diltiazem, isradipine, nicardipine, nifedipine, nimodipine, nisoldipine, nitrendipine, and verapamil. Preferably, the 5-HT$_{2A}$ antagonist is sarpogrelate. Preferably, the selective serotonin reuptake inhibitor (SSRI) is selected from the group consisting of fluoxetine, sertrlaine, paroxetine and venlafaxine. Preferably, the statin is selected from the group consisting of fluvastatin, pitavastatin, pravastatin and atorvastatin. Preferably, the vascular remodeling modulator is Gleevec.

In other preferred embodiments, therapeutic combinations are disclosed for treatment and/or prevention of stable angina. These combinations preferably include a Rho-kinase inhibitor, preferably fasudil, and sarpogrelate.

Rho-Kinase Inhibitors

Rho-kinase is involved in such processes as tumor invasion, cell adhesion, smooth muscle contraction, and formation of focal adhesion fibers, as revealed using inhibitor Y-27632. Another Rho-kinase inhibitor, 1-(5-isoquinolinesulfonyl)-homopiperazine (HA-1077 or Fasudil), is currently used in the treatment of cerebral vasospasm; the related nanomolar inhibitor H-1152P improves on its selectivity and potency. It was recently found that RhoA/Rho kinase signaling is involved in both vasoconstriction and vascular remodeling in the mouse model of hypoxic pulmonary hypertension (Fagan L. A. et al. 2004 *Am. J. Physiol. Lung Cell Mol. Physiol.* 287:L656-L664), and that Rho kinase-mediated vasoconstriction substantially contributes to the sustained elevation of pulmonary vascular resistance in rat model of hypoxic pulmonary hypertension (Nagaoka et al., 2004 *Am. J. Physiol. Lung Cell Mol. Physiol.* 287:L665-L672). In the latter study, the acute effect of intravenous Y-27632, a selective Rho-kinase inhibitor, in chronically hypoxic rats was striking (i.e., it nearly normalized the elevated pulmonary artery pressure). However, intravenous Y-27632 had no pulmonary vascular selectivity and also caused systemic vasodilation. Uehata et al. (1997, *Nature* 389:990-994) have reported that oral administration of Y-27632 has potent hypotensive effects in rat models of systemic hypertension, but has a smaller transient effect in normotensive rats. Nagaoka et al. (2005 *Am. J. Respir. Crit. Care Med.* 171:494-499) reported that 5 minutes of inhaled Y-27632 decreased mean pulmonary arterial pressure without reducing mean systemic arterial pressure. The hypotensive effect of inhaled Y-27632 on hypoxic pulmonary hypertension was greater that that of inhaled nitric oxide, and the effect lasted for at least 5 hrs. Fasudil (Asahi Kasei Pharma Co., Tokyo, Japan) is also a Rho-kinase inhibitor that is metabolized in the liver to a more specific Rho-kinase inhibitor, hydroxyfasudil, after oral administration in vivo (Shimokawa H. et al. 1999 *Cardiovasc. Res.* 43:1029-1039). Inhaled fasudil caused selective mean pulmonary arterial pressure reductions in monocrotaline-induced pulmonary hypertension and in spontaneous PH in rats, as well as in chronically hypoxic rats. In patients with severe pulmonary hypertension, fasudil, administered intravenously, significantly reduced pulmonary vascular resistance without side effects (Fukumoto Y. et al. 2005 *Heart* 91:391-392).

Improved HA-1077 analog, (S)-(+)-2-methyl-1-[(4-methyl-5-isoquinoline)sulfonyl]-homopiperazine (H-1152P), which is a more selective inhibitor of Rho-kinase, with a K(i) value of 1.6 nM for Rho-kinase was synthesized by Sasaki et al. (2002 *Pharmacol Ther.* 93:225-32). Additional specific Rho-kinase inhibitors have been synthesized by Tamura et al. (2005 *Biochim. Biophys. Acta*).

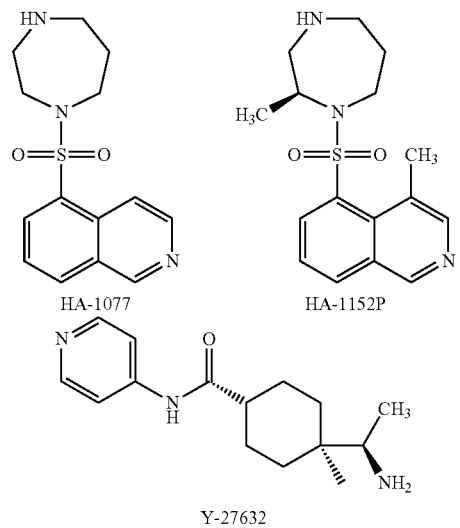

The role of Rho-kinase in cardiovascular medicine and in the treatment of stable angina is described by Shimokawa and Takeshita 2005 (*Arterioscler Thromb Vasc Biol* 25:X-X) and Hirooka and Shimokawa 2005 (*Am J Cardiovasc Drugs* 5(1): 31-39); these references are incorporated herein in their entirety by reference thereto.

HMG-CoA reductase inhibitors, known as statins, have been shown to suppress Rho-kinase activity in some systems. See e.g., Tramontano et al. 2004 (*Biochem Biophys Res Comm* 320: 34-38) and Ohnaka et al. 2001 (*Biochem Biophys Res Comm* 287: 337-342); incorporated herein in their entirety by reference thereto. Accordingly, statins such as fluvastatin, pitavastatin, pravastatin, atorvastatin, etc., may be useful in potentiating or otherwise advantageously modulating the therapeutic effect of the Rho-kinase inhibits disclosed herein.

Epoprostenol Derivatives

A continuous infusion of prostacyclin (Flolan®, GlaxoSmithKline) was the first therapy shown to reduce mortality in a controlled study of patients with severe pulmonary hypertension. However, its use is associated with a number of serious drawbacks (Barst R. J. et al. 1996 *N Engl J Med* 334:296-301; Badesch D. B. et al. 2000 *Ann Intern Med* 132:425-434). The lack of pulmonary selectivity results in systemic side effects, tolerance leads to progressive increases in the dose, and there may be recurrent infections of the intravenous catheter. As an alternative, inhaled nitric oxide possesses pulmonary selectivity, but it is less potent than prostacyclin in the pulmonary vasculature. Moreover, an interruption in the inhalation of continuous nitric oxide may cause rebound pulmonary hypertension. Designed to combine the beneficial effects of prostacyclin with those of an inhalational application, aerosolized prostacyclin was found to be a potent pulmonary vasodilator in patients with acute respiratory failure, exerting preferential vasodilatation in well-ventilated lung regions (Walmrath D. et al. 1993 *Lancet* 342:961-962; Walmrath D. et al. 1995 *Am J Respir Crit Care Med* 151:724-730; Walmrath D. et al. 1996 *Am J Respir Crit Care Med* 153:991-996; Zwissler B. et al. 1996 *Am J Respir Crit Care Med* 154:1671-1677). Similar results were obtained in spontaneously breathing patients who had lung fibrosis and severe pulmonary hypertension (Olschewski H. et al. 1999 *Am J Respir Crit Care Med* 160:600-607).

Three epoprostenol analogs have been studied in the treatment of PAH: treprostinil (Remodulin®, United Therapeutics), beraprost, and iloprost. Treprostinil is a stable analogue of epoprostenol, which is given continuously subcutaneously. Escalation of dosage has been limited by significant infusion site pain. Thus many patients do not receive therapeutic doses. Beraprost is active orally and has shown a benefit in a study in PAH at 3 and 6 months but not at 9 or 12 months (Barst, R. J. 2003 *J. Am. Coll. Cardiol.* 41:2119-25. Iloprost can be given intravenously or by nebulizer. The advantages of the nebulizer method of delivery is that less of the substance reaches the systemic circulation (a "pseudoselective" pulmonary vasodilator). Iloprost is generally given six to nine times a day, which may disrupt the patient's lifestyle; dosing frequency may be reduced by combining iloprost with an agent having a therapeutic effect on the pulmonary hypertension through a different mechanism and possibly acting synergistically.

Recently Abe K. et al. (2005 *J Cardiovasc Pharmacol* 45:120-124) demonstrated that prostacyclin and beraprost lack the inhibitory effect on Rho-kinase, when administered to rats, indicating that a combination therapy with prostacyclin and a Rho-kinase inhibitor could have further beneficial effects on pulmonary hypertension.

Iloprost

Iloprost (see U.S. Pat. No. 4,692,464; incorporated herein in its entirety by reference thereto) is a stable analogue of prostacyclin that is associated with a longer duration of vasodilatation (Fitscha P. et al. 1987 *Adv Prostaglandin Thromboxane Leukot Res* 17:450-454). When administered by aerosolization to patients with pulmonary hypertension, its pulmonary vasodilative potency was similar to that of prostacyclin, but its effects lasted for 30 to 90 minutes, as compared with only 15 minutes for the prostacyclin (Hoeper M. M. et al. 2000 *J Am Coll Cardiol* 35:176-182; Olschewski H. et al. 1999 *Am J Respir Crit Care Med* 160:600-607; Olschewski H. et al. 1996 *Ann Intern Med* 124:820-824; Gessler T. et al. 2001 *Eur Respir J* 17:14-19; Wensel R. et al. 2000 *Circulation* 101:2388-2392). Several open-label, uncontrolled studies of patients with severe pulmonary hypertension suggested that long-term use of aerosolized iloprost results in substantial clinical improvement (Olschewski H. et al. 1999 *Am J Respir Crit Care Med* 160:600-607; Olschewski H. et al. 1996 *Ann Intern Med* 124:820-824; Hoeper M. M. et al. 2000 *N Engl J Med* 342:1866-1870; Olschewski H. et al. 1998 *Intensive Care Med* 24:631-634; Stricker H. et al. 1999 *Schweiz Med Wochenschr* 129:923-927; Olschewski H. et al. 2000 *Ann Intern Med* 132:435-443; Beghetti M. et al. 2001 *Heart* 86:E10-E10). A multi-center randomized placebo controlled study of patients with severe PAH has demonstrated improved exercise capacity in patients receiving iloprost versus those receiving placebo (Olschewski H et al 2002 *NEJM* 347:322-9).

Sarpogrelate

Sarpogrelate ((φ-amino-alkoxy)phenyl-ethylethylbenzene) is a serotonin blocker, and more particularly, a selective 5-hydroxytryptamine receptor subtype 2A (5-HT$_{2A}$) antagonist. It is metabolized to racemic M-1 and both enantiomers of M-1 are also antagonists of 5-HT$_{2A}$ receptors. Sarpogrelate inhibits responses to 5-HT mediated by 5-HT$_{2A}$ receptors such as platelet aggregation, vasoconstriction and vascular smooth muscle proliferation. Sarpogrelate is efficacious in animal models of thrombosis, coronary artery spasm, atherosclerosis, restenosis, peripheral vascular disease, pulmonary hypertension, ischemic heart disease, myocardial infarction, diabetes and kidney disease (Doggrell S. A. 2004 *Expert Opin. Investig. Drugs* 13:7865-874). In the commonly used model of pulmonary hypertension, induced by monocrotaline in rat, the severity of pulmonary hypertension, determined by the medial thickness of the small pulmonary arteries and right ventricle/left ventricle and septum ration, were reduced by treatment with sarpogrelate (Miyata M. et al. 2000 *Lung* 178:63-73). Sarpogrelate also reduced the thickening of the alveolar walls and interstitial inflammatory cell infiltration. The number of proliferating cell nuclear antigen-positive cells was also reduced by sarpogrelate (Miyata M. et al. 2000 *Lung* 178:63-73).

The benefit of sarpogrelate in the monocrotaline model of pulmonary hypertension has been confirmed. Sarpogrelate, immediately following monocrotaline injection, suppressed the severe pulmonary vascular remodeling and right side heart failure and reduced mortality (Hironaka E. et al. 2003 *Cardiovasc. Res.* 60:692-629). However, late treatment with sarpogrelate failed to reverse established pulmonary hypertension. Sarpogrelate was also tested in a rat model of pulmonary embolism/pulmonary hypertension. In that model, rats injected with IL-6 develop extensive microarterial thrombosis in the lungs along with hypercoagulation and hyperfibrinolysis. The simultaneous sarpogrelate treatment in the rat prevented the IL-6-induced increase in medial thickness of small pulmonary arteries and the right ventricular hypertrophy (Miyata M. et al. 2001 *Chest* 119:554-561; Saini H. K. et al. 2004 Cardiovasc. Drug Rev. 22:27-54). Sarpogrelate has no effect on the systolic blood pressure or heart weight of spontaneously hypertensive rats (Setoguchi Y. et al. 2002 *Pharmacol.* 64:71-75).

In clinical trials, sarpogrelate significantly decreased respiratory failure and mean pulmonary arterial pressure in patients with Raynaud's phenomenon and systemic sclerosis (Kato S. et al. 2000 *Respirology* 5:27-32; Kato S. et al. 2000 *J. Int. Med. Res.* 28:258-268).

In addition, sarpogrelate has also been reported as an effective treatment for stable angina. Kinugawa et al., (*Am Heart J* 2002; 144:e1; incorporated herein in its entirety by reference thereto) had previously demonstrated that a single oral administration of sarpogrelate, a 5-HT2A receptor antagonist, may improve exercise capacity in anginal patients with well-developed collaterals. The researchers further investigated the effectiveness of 2-week treatment with sarpogrelate on anginal symptoms and exercise capacity in anginal patients.

A treadmill exercise test was repeated after a 2-week period with or without sarpogrelate (100 mg 3 times a day) in 20 patients with angiographically proven stable angina. Anginal symptoms and daily physical activity by the specific activity scale (SAS) were also evaluated. Treatment with sarpogrelate significantly increased the SAS score and prolonged exercise time to the onset of 0.1-mV ST depression. When data were analyzed in a subgroup of patients (n=8) with well-developed collaterals, the treatment with sarpogrelate decreased the number of anginal attacks (control vs sarpogrelate, 3.0±2.8 vs 0.9±1½ weeks, P<0.05), increased the SAS score (5.2±1.6 vs 6.2±1.3 METS, P<0.05), and increased the time to the onset of 0.1-mV ST depression (235±84 vs 295±127 seconds, P<0.05). In addition, the double product at the onset of 0.1-mV ST depression increased by 15% (P<0.05) after sarpogrelate. In contrast, all parameters were not significantly changed after sarpogrelate treatment in patients (n=12) without well-developed collaterals. These findings indicate the therapeutic effectiveness of sarpogrelate for anginal patients, especially for patients with well-developed collaterals.

Endothelin Receptor Antagonists (ETRA)

There is increasing evidence that endothelin-1 has a pathogenic role in pulmonary arterial hypertension and that blockade of endothelin receptors may be beneficial. Endothelin-1 is a potent endogenous vasoconstrictor and smooth-muscle mitogen that is overexpressed in the plasma and lung tissue of patients with pulmonary arterial hypertension. There are two classes of endothelin receptors: Endothelin A, ET-A and Endothelin B, ET-B receptors, which play significantly different roles in regulating blood vessel diameter. The binding of endothelin to ET-A receptors located on smooth muscle cells causes vasoconstriction, whereas the binding of endothelin to ET-B receptors located on the vascular endothelium causes vasodilatation through the production of nitric oxide. This latter activity of the ET-B receptor is thought to be counter-regulatory and protects against excessive vasoconstriction.

Therefore, another attractive approach to treating pulmonary hypertension has been the blockade of these endothelin receptors. Two types of ETRAs have been developed: dual ETRAs, which block the receptors for both ET-A and ET-B, and selective ETRAs, which block only the ET-A receptor.

a) Dual Endothelin Receptor Antagonist

The first generation ETRAs are non-selective and block both the ET-A and ET-B receptors. Bosentan (Tracleer™) is the first FDA approved ETRA (see U.S. Pat. No. 5,292,740; incorporated herein in its entirety by reference thereto). Two placebo controlled trials of bosentan (an endothelin receptor A and B antagonist) have been conducted (Channick R. N. et al. 2001 *Lancet* 358:1119-1123; Rubin L. J. et al. 2002 *N Engl J Med* 346:896-903). The six minute walk test improved in the whole group, but the improvement was greater when the drug was used in higher doses. However, liver toxicity occurred with the higher dose.

b) Selective Endothelin Receptor Antagonist

Second generation ETRAs bind to the ET-A receptor in preference to the ET-B receptor. Currently, there are two selective ETRAs in clinical trials: sitaxsentan and ambrisentan (BSF 208075). A pure endothelin A antagonist, sitaxsentan has been used in an open pilot study. This showed an improvement in the six minute walk test and a decrease in pulmonary vascular resistance of 30% (Barst R. J. et al. 2000 *Circulation* 102:II-427).

A more potent endothelin compound, TBC3711 (Encysive Pharmaceuticals), entered Phase I testing in December 2001. This drug holds potential for treating chronic heart failure and essential hypertension.

There are small clinical trials of using bosentan in patients that are already on other medications for the treatment of pulmonary hypertension (Hoeper M. M. et al. 2003 in: "Pulmonary Hypertension: Clinical", Abstr. A275, May 18, 2003; Pulmonary Hypertension Roundtable 2002, Phassociation.org/medical/advances in PH/spring 2002). In a preferred embodiment of the present invention, the combination therapy comprises fasudil, iloprost, and bosentan acting in combination through distinct mechanisms of action, preferably synergistically, to treat pulmonary hypertension. In yet another preferred embodiment, fasudil with iloprost are combined with sitaxentan. In yet another embodiment, fasudil with iloprost are combined with ambrisentan. In yet another embodiment fasudil and/or iloprost are aerosolized and administered in combination with bosentan, or sitaxentan, or ambrisentan. In another embodiment, fasudil and iloprost are combined with TBC3711 in combination therapy of pulmonary hypertension.

Nitric Oxide Production

Endothelial production of nitric oxide is diminished with pulmonary hypertension, prompting attempts to reverse this defect either by giving continuous inhaled nitric oxide, which is effective but difficult to administer, or by increasing the substrate for nitric oxide L-arginine (Nagaya N. et al. 2001 *Am J Respir Crit Care Med* 163:887-891). A trial of supplementation with L-arginine is currently under way.

PDE Inhibitors

In addition to increasing the supply of nitric oxide, attempts to directly increase cyclic nucleotide second messenger levels in the smooth muscle cells have been made. Sildenafil used for erectile dysfunction blocks the enzyme phosphodiesterase type 5 present in the corpus cavernosum of the penis and also the lungs. This raises the possibility that a phosphodiesterase inhibitor, preferably a PDE type 5 inhibitor such as sildenafil, could be a relatively selective pulmonary vasodilator. There is empirical evidence supporting the inventor's selection of PDE inhibitors as a target compound in a combination therapy (see e.g., Michelakis E. et al. 2002 *Circulation* 105:2398-2403; Ghofrani H. et al. 2002 Lancet 360:895-900; the disclosures of which are incorporated herein in their entirety by reference).

Although aerosolized prostacyclin ($PGI_2$) has been suggested for selective pulmonary vasodilation as discussed above, its effect rapidly levels off after termination of nebulization. Stabilization of the second-messenger cAMP by phosphodiesterase (PDE) inhibition has been suggested as a strategy for amplification of the vasodilative response to nebulized $PGI_2$. Lung PDE3/4 inhibition, achieved by intravascular or transbronchial administration of subthreshold doses of specific PDE inhibitors, synergistically amplified the pulmonary vasodilatory response to inhaled $PGI_2$, concomitant with an improvement in ventilation-perfusion matching and a reduction in lung edema formation. The combination of nebulized $PGI_2$ and fasudil with PDE3/4 inhibition may thus offer a new concept for selective pulmonary vasodilation, with maintenance of gas exchange in respiratory failure and pulmonary hypertension (Schermuly R. T. et al. 2000 *J Pharmacol Exp Ther* 292:512-20). There are some reports of small clinical studies showing that such combination therapy may be efficacious in the treatment of pulmonary hypertension (Ghofrani et al. 2002 *Crit Care Med* 30:2489-92; Ghofrani et al. 2003 *J Am Coll Cardiol* 42:158-164; Ghofrani et al. 2002 *Ann Intern Med* 136:515-22).

Isozymes of cyclic-3',5'-nucleotide phosphodiesterase (PDE) are a critically important component of the cyclic-3', 5'-adenosine monophosphate (cAMP) protein kinase. A (PKA) signaling pathway. The superfamily of PDE isozymes consists of at least nine gene families (types): PDE1 to PDE9. Some PDE families are very diverse and consist of several subtypes and numerous PDE isoform-splice variants. PDE isozymes differ in molecular structure, catalytic properties, intracellular regulation and location, and sensitivity to selective inhibitors, as well as differential expression in various cell types.

A phosphodiesterase (PDE) inhibitor is defined herein as any drug used in the treatment of pulmonary arterial hypertension that works by blocking the inactivation of cyclic AMP. There are five major subtypes of phosphodiesterase (PDE); the drugs enoximone (inhibits PDE IV) and milrinone (Primacor®) (inhibits PDE IIIc) are most commonly used medically. Other phosphodiesterase inhibitors include Amrinone (Inocor®) used to improve myocardial function, pulmonary and systemic vasodilation, and sildenafil (Viagra®), tadalafil (Clalis®) and vardenafil (LEVITRA®)—selective phosphodiesterase V inhibitors.

Calcium Channel Blockers

In accordance with one embodiment of the present invention, a Rho-kinase inhibitor, preferably fasudil, is administered in combination with a second agent, which is a calcium channel blockers. Calcium channel blockers, or antagonists, act by blocking the entry of calcium into muscle cells of heart and arteries so that the contraction of the heart decreases and the arteries dilate. With the dilation of the arteries, arterial pressure is reduced so that it is easier for the heart to pump blood. This also reduces the heart's oxygen requirement. Calcium channel blockers are useful for treating PPH. Due to blood pressure lowering effects, calcium channel blockers are also useful to treat high blood pressure. Because they slow the heart rate, calcium channel blockers may be used to treat rapid heart rhythms such as atrial fibrillation. Calcium channel blockers are also administered to patients after a heart attack and may be helpful in treatment of arteriosclerosis.

Calcium channel blockers which are within the scope of this invention include, but are not limited to: amlodipine (U.S. Pat. No. 4,572,909); bepridil (U.S. Pat. No. 3,962,238); clentiazem (U.S. Pat. No. 4,567,175); diltiazem (U.S. Pat. No. 3,562,257); fendiline (U.S. Pat. No. 3,262,977); gallopamil (U.S. Pat. No. 3,261,859); mibefradil (U.S. Pat. No. 4,808,605); prenylamine (U.S. Pat. No. 3,152,173); semotiadil (U.S. Pat. No. 4,786,635); terodiline (U.S. Pat. No. 3,371,014); verapamil (U.S. Pat. No. 3,261,859); aranidipine (U.S. Pat. No. 4,446,325); bamidipine (U.S. Pat. No. 4,220,649): benidipine (European Patent Application Publication No. 106,275); cilnidipine (U.S. Pat. No. 4,672,068); efonidipine (U.S. Pat. No. 4,885,284); elgodipine (U.S. Pat. No. 4,952,592); felodipine (U.S. Pat. No. 4,264,611); isradipine (U.S. Pat. No. 4,466,972); lacidipine (U.S. Pat. No. 4,801,599); lercanidipine (U.S. Pat. No. 4,705,797); manidipine (U.S. Pat. No. 4,892,875); nicardipine (U.S. Pat. No. 3,985,758); nifedipine (U.S. Pat. No. 3,485,847); nilvadipine (U.S. Pat. No. 4,338,322); nimodipine (U.S. Pat. No. 3,799,934); nisoldipine (U.S. Pat. No. 4,154,839); nitrendipine (U.S. Pat. No. 3,799,934); cinnarizine (U.S. Pat. No. 2,882,271); flunarizine (U.S. Pat. No. 3,773,939); lidoflazine (U.S. Pat. No. 3,267,104); lomerizine (U.S. Pat. No. 4,663,325); bencyclane (Hungarian Patent No. 151,865); etafenone (German Patent No. 1,265,758); and perhexiline (British Patent No. 1,025,578). The disclosures of all such patents and patent applications are incorporated herein by reference.

Preferred calcium channel blockers comprise amlodipine, diltiazem, isradipine, nicardipine, nifedipine, nimodipine, nisoldipine, nitrendipine, and verapamil, or, e.g., dependent on the specific calcium channel blockers, a pharmaceutically acceptable salt thereof.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having at least one acid group (for example COOH) can also form salts with bases. Corresponding internal salts may furthermore be formed, if a compound of formula comprises e.g., both a carboxy and an amino group.

In accordance with one preferred embodiment of the present combination therapy, fasudil and iloprost are administered together with a second generation calcium antagonist, such as amlodipine. The combination may be administered in a sustained release dosage form. Preferably, the combination dosage and release form is optimized for the treatment of hypertensive patients.

Gleevec

Recently, Gleevec (Imatinib) has been shown to be successfully used in two well established experimental models of progressive pulmonary arterial hypertension. It was found that the treatment resulted in virtually complete reversal of lung vascular remodeling, pulmonary hypertension and right heart hypertrophy.

In the Sep. 29, 2005 issue of the New England Journal of Medicine, a 61-year-old man suffering from an advanced case of the disease saw his condition improve and stabilize after taking Gleevec (imatinib)—even though all other medications had failed. "Only the addition of Gleevec was able to prevent further deterioration, and even improved his condition," said co-researcher Dr. Hossein A. Ghofrani, of University Hospital Giessen, in Germany. Although a single case report does not warrant widespread use of Gleevec for pulmonary hypertension, the German researchers who wrote the report said they are now planning a large clinical trial. Accordingly, Applicant considers Gleevec to be a potential additional ingredient in the combination therapies disclosed herein.

The therapeutic combinations disclosed herein for the treatment and/or prevention of PAH and/or stable angina are combinations of known drugs. The pharmacologic properties of these drugs are well known to the skilled practitioner. The combinations may be formulated or otherwise individually administered such that the relative amounts of each drug in the combination is sufficient, when combined to treat and/or prevent at least one symptom associated with PAH and/or stable angina. The symptoms of PAH and stable angina are well known. Moreover, animal models of these conditions may be used to optimize dosages (see e.g., the references cited and incorporated herein). The skilled practitioner will be able to determine without undue experimentation optimal dosages. It is likely that lower doses, for example of fasudil in combination with iloprost or sarpogrelate, may be used in the recited combinations because the individual agents may interact in additive or synergistic manners, and preferably, the individual agents target independent mechanisms of action.

It is understood that all drugs disclosed as potential candidates for the recited combination therapies may be used in their free forms or as salts thereof. It is also understood that the recitation of therapeutic combinations and methods of treatment include active metabolites, formed in vivo, which are known in the art for the disclosed candidate drugs.

The drugs in the recited therapeutic combinations can be administered, as described herein, according to any of a number of standard methods including, but not limited to injection, suppository, nasal spray, time-release implant, transdermal patch, and the like. In particularly preferred embodiments, at least one of the drugs in the combination is administered orally (e.g. as a syrup, capsule, or tablet) or by inhalation (either as a dry powder formulation or as a nebulized formulation). In one preferred embodiment, fasudil, hydroxyfasudil, or salts thereof, may be given orally. More preferably, the fasudil, hydroxyfasudil, or salts thereof, is administered as a sustained-release formulation sufficient to provide extended plasma half-life and minimize the peaks and troughs of plasma concentrations between dosing. Such formulations are well known in the art and may enhance bioavailability of the drug. In another preferred embodiment, fasudil, hydroxyfasudil, or salts thereof, may be administered by inhalation.

More generally, injectable preparations include sterile suspensions, solutions or emulsions of the active ingredients in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, stored preparations can be supplied in unit dosage forms and reconstituted prior to use in vivo.

For prolonged delivery, the active ingredients can be formulated as a depot preparation, for administration by implantation; e.g., subcutaneous, intradermal, or intramuscular injection. Thus, for example, the active ingredient may be formulated with suitable polymeric or hydrophobic materials (e.g., as an emulsion in an acceptable oil) or ion exchange resins, or as sparingly soluble derivatives; e.g., as a sparingly soluble salt form of the candidate drugs.

Alternatively, transdermal delivery systems manufactured as an adhesive disc or patch which slowly releases the active ingredient for percutaneous absorption may be used. To this end, permeation enhancers may be used to facilitate transdermal penetration of the active ingredients.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration, the compositions may take the form of tablets or lozenges formulated in conventional manner. For rectal and vaginal routes of administration, the active ingredients may be formulated as solutions (for retention enemas) suppositories or ointments.

For administration by inhalation, the active ingredients can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compositions may, if desired, be presented in a pack or dispenser device which may contain one or more unit dosage forms containing the active ingredients. The pack may for example comprise metal or plastic foil, such as a blister pack. The pack or dispenser device may be accompanied by instructions for administration.

EXAMPLE 1

Isolated PA Rings

Small (4th or 5th branch) pulmonary arteries (SPA, 200-300 µm ID) were isolated from rats exposed to chronic hypoxia (~10% oxygen) for 3 to 4 weeks. Briefly, after anesthesia with pentobarbital sodium (30 mg ip) and heparinization (100 IU), the heart and lungs were removed en bloc, and the SPA were isolated under a dissecting microscope. Care was taken to avoid damage to the endothelium. The SPA rings were placed on steel wires attached to a force transducer and suspended in baths containing 10 ml of physiological salt solution (PSS) at 37° C. Resting passive force was adjusted to a previously determined optimal tension (determined by maximum response to 80 mM KCl: 400 mg for SPA from normotensive lungs (NL), and 750 mg for SPA from hypoxic hypertensive lungs (HL). Rings were gassed with 21% $O_2$-5% $CO_2$-74% $N_2$ and allowed to equilibrate for 60 min. The artery rings were then constricted with a combination of endothelin-1 (ET-1) (3 nM) plus thromboxane analogue U46619 (30 nM) plus 5-HT (3 µM). After the vasoconstrictor-induced constriction of the pulmonary artery rings had reached a plateau, the various vasodilators (iloprost, bosentan, sildenafil (Viagra™) or fasudil) were added individually to the muscle baths to achieve a calculated concentration. When the vasodilator response to the first concentration of drug had reached a plateau, additional vasodilator was added to the bath to achieve the next higher concentration, and so on until the highest concentration used was reached to obtain dose-response curves for each compound individually. Then, after the highest concentrations of iloprost, bosentan, and sildenafil were tested, increasing concentrations of fasudil were added sequentially to the same baths to obtain dose-response curves for fasudil in the presence of the tested compounds. FIGS. 1-3 show the obtained dose-response curves.

EXAMPLE 2

Isolated PA Rings

The experiments are performed essentially as described above, but the rings are constricted with each of the vasoconstrictors individually. The dose response curves of fasudil with iloprost, fasudil with bosentan, fasudil with sildenafil show synergistic effects on the relaxation of the PA rings.

EXAMPLE 3

Conscious Catheterized Rats

Experiments are performed with a chronically hypoxic, pulmonary-hypertensive group of rats which have been exposed to hypobaric hypoxia (410 mmHg barometric pressure, 76 mmHg inspired $O_2$ tension) for 3-4 wk in a chamber flushed continuously with room air to prevent accumulation of $CO_2$, $NH_3$, and $H_2O$. Hypobaric exposure has been 24 h/day, except when the chamber has been opened for 10-15 min every 2 days to remove rats or clean cages and replenish food and water. All rats are exposed to a 12:12-h light-dark cycle and allowed free access to standard rat food and water.

The chronically hypoxic rats are anesthetized with ketamine (100 mg/kg) and xylazine (15 mg/kg) for placement of catheters in the right jugular vein and pulmonary and right carotid arteries (Oka M. 2001 *Am J Physiol Lung Cell Mol Physiol* 280: L432-L435). The rats are allowed to recover for 48 h in room air. After recovery, conscious rats are placed in a ventilated plastic box, and pulmonary and systemic arterial pressures are measured with pressure transducers. Cardiac output is determined by a standard dye-dilution method, and total pulmonary resistance (TPR) is calculated by dividing mean PA pressure (MPAP) by cardiac output. The rats are then injected with various doses of vasodilators, such as iloprost, bosentan or sildenafil alone or in combination with fasudil at 30-min intervals between doses. Pressures are measured 10 min after injection of each dose. Cardiac output measurements are repeated 10 min after injection of the lowest and the highest doses tested for each compound. After the final dose, rats are again exposed to 10 min of hypoxia. The combinations show synergistic effects on the MPAP and TPR of the chronically hypoxic rats.

EXAMPLE 4

Isolated Perfused Lungs

After pulmonary-hypertensive rats are removed from the hypobaric chamber and anesthetized with pentobarbital sodium (30 mg i.p.), lungs are isolated and perfused for vasoreactivity studies. The techniques of lung isolation, ventilation, and perfusion have been described in detail elsewhere (Morio Y. & McMurtry I. F. 2002 *J Appl Physiol* 92:527-534). The perfusate is 20 ml of PSS. Ficoll (4 g/100 ml; type 70, Sigma) is included as a colloid, and 3.1 μM meclofenamate (Sigma) is added to inhibit synthesis of vasodilator prostaglandins. Perfusion rate is 0.04 ml·g body $wt^{-1} \cdot min^{-1}$. PSS-perfused hypoxic hypertensive lungs (HL) are equilibrated at 37° C. for 20 min during ventilation with 8% $O_2$-5% $CO_2$-87% $N_2$. After equilibration, two hypoxic pressor responses are elicited by 10 min of ventilation with 0% $O_2$-5% $CO_2$-95% $N_2$ and 3% $O_2$-5% $CO_2$-92% $N_2$, separated by 10 min of normoxic ventilation, to induce hypoxic vasoreactivity. The drugs are added to the perfusate reservoir to achieve the calculated circulating concentrations. The vasoconstriction is achieved by Nomega-nitro-L-arginine (L-NNA), a NO synthase (NOS) inhibitor. After development of the L-NNA-induced vasoconstriction, iloprost, bosentan, sildenafil, or fasudil alone, or iloprost, bosentan, sildenafil each in combination with fasudil are added cumulatively to the perfusate of separate lungs at 10-min intervals. The baseline perfusion pressure is measured before and after the vasodilators. The combinations of the tested drugs showed synergistic effects on the reduction of the baseline perfusion pressure.

While a number of preferred embodiments of the invention and variations thereof have been described in detail, other modifications and methods of using the disclosed therapeutic combinations will be apparent to those of skill in the art. Accordingly, it should be understood that various applications, modifications, and substitutions may be made of equivalents without departing from the spirit of the invention or the scope of the claims. Further, it should be understood that the invention is not limited to the embodiments set forth herein for purposes of exemplification, but is to be defined only by a fair reading of the appended claims, including the full range of equivalency to which each element thereof is entitled.

REFERENCES

1. Kato et al. (2000) *Respirology* 5:
2. Kato et al. (2000) *J. Int. Med. Res.* 28: 258-268.
3. Doggrell (2004) *Expert Opin. Investig. Drugs* 13: 7865-874.
4. Saini et al (2004) *Cardiovasc. Drug Rev.* 22: 27-54.
5. Abe et al. (2005) *J Cardiovasc Pharmacol* 45:120-124.
6. Nagaoka et al. (2004) *Am. J. Physiol. Lung Cell Mol. Physiol.* 287: L665-L672.
7. Fukumoto et al. (2005) *Heart* 91: 391-392.
8. Takemoto et al. (2002) *Circulation* 106: 57-62.
9. Abe et al. (2004) *Circ Res* 94: 385-393.
10. Tramontano et al. (2004) *Biochem Biophys Res Comm* 320: 34-38.
11. Ohnaka et al. (2001) *Biochem Biophys Res Comm* 287: 337-342.
12. Shimokawa et al. (1999) *Cardiovasc. Res.* 43:1029-1039.
13. Hirooka et al. (2005) *Am J Cardiovasc Drugs* 5(1): 31-39.

All of the references cited herein are incorporated in their entirety by reference thereto.

What is claimed is:

1. A therapeutic combination comprising an effective amount of fasudil and bosentan.

2. The therapeutic combination of claim 1, wherein the fasudil and the bosentan are formulated independently.

3. The therapeutic combination of claim 1, wherein the fasudil is formulated for administration via inhalation.

4. The therapeutic combination of claim 3, wherein the fasudil is formulated in a dry powder or an aerosolizable solution.

5. A method for treating pulmonary arterial hypertension in a person in need of such treatment comprising administering to a person in need thereof a therapeutically effective amount of a combination of fasudil and bosentan.

6. The method according to claim 5, wherein the fasudil and the bosentan are administered in separate dosage forms.

7. The method according to claim 5, wherein the fasudil is administered by inhalation.

8. The method according to claim 7, wherein the fasudil is administered in a dry powder or an aerosolizable solution.

* * * * *

UNITED STATES PATENT AND TRADEMARK OFFICE
CERTIFICATE OF CORRECTION

| | | |
|---|---|---|
| PATENT NO. | : 8,476,259 B2 | Page 1 of 1 |
| APPLICATION NO. | : 13/611849 | |
| DATED | : July 2, 2013 | |
| INVENTOR(S) | : B. Fong | |

It is certified that error appears in the above-identified patent and that said Letters Patent is hereby corrected as shown below:

On the Title page, item 75, (inventor), please change "Benson Fong" to --Benson M. Fong--.

Signed and Sealed this
Twenty-eighth Day of January, 2014

Michelle K. Lee
*Deputy Director of the United States Patent and Trademark Office*